United States Patent [19] [11] 4,044,069
Bernard et al. [45] Aug. 23, 1977

[54] CATALYTIC COMPOSITION FOR THE ISOMERIZATION AND ALKYLATION OF HYDROCARBONS

[75] Inventors: Jean René Bernard, St-Symphorien d'Ozon; Daniel Elie Brunel, Montpellier; Auguste André Commeyras, Clapiers; Camille Michel Coste, Amelie-Les-Bains; Jean Joseph Itier, Montpellier; Hubert Wilhelm Knoche, Meyzieu, all of France

[73] Assignee: Societe Nationale Elf Aquitaine, Courbevoie, France

[21] Appl. No.: 656,902

[22] Filed: Feb. 10, 1976

Related U.S. Application Data

[62] Division of Ser. No. 509,608, Sept. 26, 1974, Pat. No. 3,960,764.

[30] Foreign Application Priority Data

Sept. 26, 1973 France .............................. 73.34561

[51] Int. Cl.$^2$ .......................... C07C 3/54; C07C 5/24
[52] U.S. Cl. .......................... 260/683.47; 260/683.68
[58] Field of Search .................. 260/683.68, 683.47, 260/683.58, 666 P

[56] References Cited

U.S. PATENT DOCUMENTS

| | | | |
|---|---|---|---|
| 3,594,445 | 7/1971 | Parker | 260/683.68 |
| 3,678,120 | 7/1972 | Bloch | 260/683.47 |
| 3,708,553 | 1/1973 | Olah | 260/683.47 |
| 3,839,489 | 10/1974 | Mahan et al. | 260/683.68 |
| 3,855,346 | 12/1974 | Norell | 260/683.68 |
| 3,960,764 | 6/1976 | Bernard et al. | 260/683.68 |

*Primary Examiner*—George Crasanakis
*Attorney, Agent, or Firm*—Sughrue, Rothwell, Mion, Zinn and Macpeak

[57] ABSTRACT

A catalytic composition is employed for the isomerization of paraffins and the alkylation of paraffins with olefins.

The composition is constituted by a mixture of Lewis acid corresponding to the formula $MX_m$ where:
  M is an atom of a metal belonging to Groups IV, V and VI of the Periodic Table of Elements,
  X is a halogen,
  $m$ is within the range of 3 to 6,
  and a sulphonic acid corresponding to the general formula $RF(SO_3H)p$ where RF represents a perfluorinated alkyl or cycloalkyl hydrocarbon radical having a number of carbon atoms ranging from 2 to 8 and $p$ is 1 or 2.

15 Claims, No Drawings

[4,044,069]

CATALYTIC COMPOSITION FOR THE ISOMERIZATION AND ALKYLATION OF HYDROCARBONS

CROSS REFERENCE TO RELATED APPLICATION

This application is a divisional application of U.S. application Ser. No. 509,608, filed Sept. 26, 1974, now U.S. Pat. No. 3,960,764 Bernard et al entitled "A Catalytic Composition For The Conversion Of Hydrocarbons".

BACKGROUND OF THE INVENTION

1. Field of the Invention

This invention relates to a catalytic composition which can be employed for the conversion of petroleum products and in particular for isomerization, alkylation, dealkylation and polymerization of hydrocarbons; the invention further relates to a corresponding method of conversion.

2. Description of the Prior Art

It is known that in the field of petroleum refining, many conversion processes are carried out by means of catalysts and have an acid character. Acid catalysts which can be mentioned by way of example include aluminosilicate, the zeolites, aluminum chloride and bromide, the chlorinated aluminas and the liquid mineral acids such a sulphuric acid, hydrofluoric acid and phosphoric acid.

Recent researches have led investigators to develop superacid catalysts.

As disclosed in French Pat. No. 2,005,043, the isomerization of aliphatic hydrocarbons containing at least five carbon atoms can be carried out by means of an acid catalyst constituted by a combination of hydrofluoric acid and antimony pentafluoride in the presence of hydrogen.

The isomerization of normal and naphthenic paraffins has been performed in accordance with the method described in U.S. Pat. No. 3,594,445 by employing a catalyst containing (1) a fluoride of metal of Group V such as antimony pentafluoride and (2) a fluorosulphonic acid in the presence of hydrogen and of an olefin and/or of an alkylfluorosulphonate.

Another catalyst which is used for isomerization, alkylation and polymerization has been described in U.S. Pat. No. 3,678,120. This catalyst comprises antimony pentafluoride and hydrofluoric acid or a fluorosulphonic acid.

Finally, it is disclosed in U.S. Pat. No. 3,708,553 that the alkylation of hydrocarbons can be carried out by means of a catalyst consisting of a Lewis acid and a strong acid selected from fluorosulphonic acid and trifluoromethanesulphonic acid.

SUMMARY OF THE INVENTION

There has now been discovered a novel catalytic composition which is intended to be employed in reactions involving the conversion of aliphatic hydrocarbons and considerably improves the efficiency of such reactions.

The invention is directed to a catalytic composition for the conversion of hydrocarbons under conditions suited to the conversion which is sought, said composition being constituted by a mixture of Lewis acids and a sulphonic acid corresponding to the general formula $R_F(SO_3H)_p$ where $R_F$ represents an alkylperfluorinated or cycloalkylperfluorinated hydrocarbon radical having a number of carbon atoms between 2 and 8 and $p$ is 1 or 2.

A perfluorinated radical is understood to mean a hydrocarbon radical in which fluorine atoms are substituted for the hydrogen atoms.

DETAILED DESCRIPTION OF THE INVENTION

In the description which now follows, the term "protonic acid" will be employed to designate the sulphonic acids in accordance with the invention and considered as a whole.

The protonic acids according to the invention are selected from:

perfluorinated alkylsulphonic acids having the formula $C_n F_{(2n+1)} SO_3 H$ where $n$ is within the range of 2 to 8;

perfluorinated alkyldisulphonic acids having the formula $C_n F_{2n} (SO_3 H)_2$ where $n$ is within the range of 2 to 8;

perfluorinated cycloalkylsulphonic acids having the formula $C_n F_{(2n-1)} (SO_3 H)$ where $n$ is within the range of 5 to 8.

The catalytic composition of the invention is constituted by the mixture of a protonic acid precisely as hereinabove defined and a Lewis acid.

It will be understood that, although it is the customary practice to make use of a single Lewis acid, a mixture of several of these acids may nevertheless be employed.

The Lewis acid used in the composition according to the invention is a metal halide corresponding to the formula:

$$M X_m$$

where

M is an atom of a metal which belongs to Groups IV, V and VI of the Periodic Table of Elements and preferably to Group V of said Periodic Table;
X is a halogen and preferably fluorine;
$m$ is within the range of 3 to 6.

The following Lewis acids which can be employed in the catalytic composition can be mentioned by way of example:

arsenic pentafluoride, tantalum pentafluoride, vanadium pentafluoride, zirconium tetrafluoride, antimony pentafluoride, molybdenum hexafluoride. Antimony pentafluoride is preferably selected from all these acids.

As a general rule, the catalytic composition comprises from 0.1 to 10 and preferably from 0.5 to 5 moles of Lewis acid in respect of one mole of protonic acid having the formula $R_F(SO_3H)_p$.

In order to achieve enhanced catalytic activity, it appears desirable to carry out the reaction in the presence of a small excess quantity of Lewis acid. The molar ratio $$\frac{\text{Lewis acid}}{\text{protonic acid}}$$

is preferably within the range of 1 to 3.

In the various methods of conversion of hydrocarbons, the catalytic composition in accordance with the invention can by employed either in liquid form or in solid form.

If the liquid catalysts are active, it is often advantageous to make provision for a solid catalyst since this facilitates the separation of the charge from the catalyst, especially if this latter does not rapidly become fouled.

A catalyst is usually constituted by an inert solid support in which the active material has been introduced in a suitable manner. For example, in the conventional methods of alkylation of paraffins and of polymerization of olefins, it is a frequent practice to make use of an active liquid agent such as sulphuric acid or phosphoric acid deposited on a solid support such as silica of silica-alumina.

The catalytic composition in accordance with the invention can be employed with all the supports which are suited to the catalyst. It is preferably, however, to select this support with care since the catalyst essentially has a high acid strength and accordingly destroys many conventional supports, thereby reducing its acidity and therefore partially de-activating the catalyst. In order to overcome this disadvantage, supports are chosen so as to ensure that they do not block the acidity of the catalyst and are inert with respect to the active material.

In order to select suitable inert supports, they are subjected to a test which consists in measuring after 15 minutes the degree of conversion of a charge of n-hexane passing through a support impregnated with a 2/1 molar mixture of antimony pentafluoride (SbF5) and of sulphonic trifluoromethane ($CF_3SO_3H$).

The operating conditions of the test are:

| | | |
|---|---|---|
| Temperature | : | 50° C |
| $\frac{\text{Volume of charge (hexane)}}{\text{Volume of catalyst}}$ per hour | : | 30 |
| Pressure | : | 1 Atm. |

If the support is not inert with respect to the active material, the conversion of n-hexane after 15 minutes is practically zero and the quality of the tested support is measured by the degree of conversion.

This test makes it possible to select excellent supports such as calcium fluoride ($CaF_2$), polytetrafluoroethylene, fluorinated carbon ($CF_{0.9}$), aluminum trifluoride ($AlF_3$).

The catalyst according to the invention can be employed in many methods of conversion of hydrocarbons such as isomerization, cracking, polymerization, alkylation and so forth.

When these different methods are carried out in practice, compounds which are intended to inhibit undesirable secondary reactions are usually added to the reaction medium. The choice of said compounds naturally depends on the nature of the conversion which is sought. The following inhibitors can be mentioned by way of example: hydrogen, olefins, benzene, alkyl-fluorosulphonates.

The catalytic composition in accordance with the invention produces excellent results in the isomerization and alkylation of hydrocarbons having a number of carbon atoms within the range of 4 to 8.

The invention is illustrated by means of the following practical examples which relate to isomerization from n-pentane to isopentane and to alkylation of isobutane with propylene.

Among the four first examples in which the results are recorded in Table I below, Examples I and II result from the use of catalysts which are already known and have the respective formulae $SbF_5$, $FSO_3H$ and $SbF_5$, $CF_3SO_3H$. Examples III and IV are carried into effect with catalytic compositions in accordance with the invention and containing catalysts having the respective formulae:

$$SbF_5, C_4F_9SO_3H$$

and $$SbF_5, C_6F_{13}SO_3H.$$

In these four examples, the operation is carried out as follows: in an autoclave having a capacity of 12.5 ml, there are introduced 7.5 ml of n-pentane (number of moles: 0.065) and a mixture in a ratio of 2:1 of antimony pentafluoride (number of moles: 0.00250) and perfluorinated sulphonic acid (number of moles: 0.00125), the entire quantity being then subjected to a pressure of 5 bars of hydrogen. The autoclave is shaken for a period of 45 minutes at a temperature of 80° C. The reaction products are analyzed by gas-phase chromatography.

TABLE I

| | | Percentage of hydrocarbons formed | | | | | | |
|---|---|---|---|---|---|---|---|---|
| | | Light products | | Light products | | | Heavy products | Ratio Iso $C_5$ |
| Examples | Catalysts | iso $C_4$ | $nC_4$ | Total | iso $C_5$ | $nC_5$ | $C_6 - C_9$ | $nC_5$ |
| I | $SbF_5, FSO_3H$ | — | — | — | 10 | 90 | — | 0.11 |
| II | $SbF_5, CF_3SO_3H$ | 14 | 3 | 17 | 28 | 45 | 10 | 0.62 |
| III | $SbF_5, C_4F_9SO_3H$ | 15 | 4.5 | 19.5 | 36 | 29.5 | 14 | 1.22 |
| IV | $SbF_5, C_6F_{13}SO_3H$ | 22 | 6.5 | 28.5 | 36.5 | 15.5 | 18.5 | 2.36 |

Analysis of the values obtained shows that:

1. the ratio ($^{iso}C_5$)/$nC_5$ which is representative of the reaction of isomerization from $nC_5$ to iso $C_5$ increases with the lengthening of the fluorocarbon chain which carries the $SO_3H$ function.

2. the undersirable reactions of cracking and dismutation increase in the same manner.

In Examples V to XIII, the results of which are recorded in Table II below, the operation is performed as follows:

The catalyst and a charge of 99.5% by weight of n-pentane are placed in a Duralumin autoclave fitted with an agitating system and a loop which permits frequent chromatographic analysis. The reaction vessel, the charge and the catalyst are carefully dried and protected against humidity. The reaction is carried out at room temperature at approximately 25° C in an atmosphere containing nitrogen and hydrogen. In general, isomerization reactions are conducted at fairly low temperature within the range of −10° to 100° C.

TABLE II

| Examples | RF(SO$_3$H)$_p$ | molar ratio SbF$_5$/ RF(SO$_3$H)$_p$ | weight catalyst (g) | weight charge (g) | total pressure (bars) | pressure H$_2$ (bars) | times of reaction (hours) | percentages by weight of hydrocarbons formed | | | |
|---|---|---|---|---|---|---|---|---|---|---|---|
| | | | | | | | | light products | iC$_5$ | nC$_5$ | heavy products |
| V | C$_2$F$_5$SO$_3$H | 1.85 | 3.15 | 21.7 | 7 | 2 | 5.5 | 0 | 50 | 50 | 0 |
| | | | | | | | 10 | 1 | 76 | 24 | 0 |
| | | | | | | | 12 | 1.5 | 80 | 18.5 | 1 |
| | | | | | | | 16 | 31 | 37 | 12.5 | 20 |
| | | | | | | | 24 | 50.5 | 21 | 4.5 | 24 |
| VI | C$_2$F$_5$SO$_3$H | 1.85 | 2.75 | 21.7 | 7 | 4 | 6.5 | 0 | 50 | 50 | 0 |
| | | | | | | | 12 | 2 | 77.5 | 19 | 1.5 |
| | | | | | | | 18 | 6.5 | 77.5 | 11 | 5 |
| | | | | | | | 30 | 47 | 22.5 | 4 | 27 |
| VII | C$_4$F$_9$SO$_3$H | 1.98 | 2.83 | 21.7 | 7 | 0.013 | 3 | 0 | 33 | 67 | 0 |
| | | | | | | | 4.5 | 2 | 45 | 47 | 1 |
| | | | | | | | 8 | 27.5 | 27.5 | 27.5 | 18 |
| | | | | | | | 20 | 44 | 23 | 11 | 23 |
| VIII | C$_4$F$_9$SO$_3$H | 1.88 | 2.15 | 21.7 | 7 | 2 | 4 | 0 | 32 | 68 | 0 |
| | | | | | | | 6 | 4 | 52 | 40 | 5 |
| | | | | | | | 10 | 35 | 28 | 16 | 21 |
| IX | C$_4$F$_9$SO$_3$H | 1.88 | 2.09 | isopentane (alone) 21.7 | 7 | 1 | 4 | 7 | 86 | 1.5 | 5.5 |
| | | | | | | | 10 | 17.5 | 66.5 | 2. | 13.5 |
| | | | | | | | 30 | 31 | 42.5 | 2.5 | 23 |
| X | C$_6$F$_{13}$SO$_3$H | 1.71 | 2.45 | 21.7 | 7 | 2 | 4 | 0 | 19.5 | 80.5 | 0 |
| | | | | | | | 3 | 6 | 36.5 | 55.5 | 3 |
| | | | | | | | 12 | 23 | 28.5 | 34 | 15.5 |
| XI | C$_4$F$_9$SO$_3$H | 1.96 | | 21.7 | 7 | 6 | 4 | | 50 | 50 | |
| | | | | | | | 8 | | 76.5 | 23.5 | |
| | | | | | | | 12 | 2.5 | 80. | 16 | 1.5 |
| | | | | | | | 17 | 35.5 | 35.5 | 13 | 16 |
| XII | C$_2$F$_4$(SO$_3$H)$_2$ | 1.2 | 2.43 | 21.7 | 7 | 3 | 6 | 0 | 45 | 55 | 0 |
| | | | | | | | 10 | 3 | 76 | 19 | 2 |
| | | | | | | | 20 | 38 | 22 | 11 | 30 |
| XIII | C$_6$F$_{11}$SO$_3$H | 1.8 | 2.52 | 21.7 | 7 | 2 | 4 | 0 | 25 | 75 | 0 |
| | | | | | | | 9 | 2 | 45.5 | 51.5 | 1 |
| | | | | | | | 13 | 15 | 68 | 5 | 12 |

It is pointed out that, in the sulphonic acid of Example XII, C$_2$F$_4$(SO$_3$H), the SO$_3$H acid functions are carried by two different carbon atoms and that sulphonic acid C$_6$F$_{11}$(SO$_3$H) is sulphonic perfluorocyclohexane acid.

It should be explained that the light products are n-butane and isobutane and that the heavy products are the different isomers of paraffins having carbon atoms within the range or 6 to 9.

In Example IX, the reaction was conducted on isopentane simply by way of experiment in order to study the proportions of gases formed which it is not sought to obtain and which are constituted by n-pentane and light and heavy gases.

If a comparison is drawn especially between the results of Example VII and IX, it is observed that hydrogen has a favorable influence on isomerization since 25.5% by weight of isopentane are found in Example VII at the end of 8 hours whereas there are only 76.5 % by weight in Example XI.

EXAMPLE XIV

In a steel autoclave, there were introduced 4.5 g of antimony pentafluoride and 2.4 g of sulphonic perfluoroethane acid (C$_2$F$_5$SO$_3$H). The catalyst was brought to 0° C and a mixture of 30 g of isobutane and 4.5 g of propylene was allowed to react for a period of 1 hour with agitation. After the reaction, the reactor was reheated to room temperature and expanded to atmospheric pressure. There were then collected 22 g of gas containing 98% of isobutane and 1.5 % by weight of propylene (percentages by weight). The liquid phase was treated with water and then decanted. There were finally collected 10.6 g of hydrocarbon liquid containing the following percentages by weight:

| | |
|---|---|
| isobutane | 2.8 % |
| C$_5$ | 8.4 % |
| C$_6$ | 11.9 % |

-continued

| | |
|---|---|
| C$_7$ | 19.7 % |
| C$_8$ | 44.0 % |
| C$_9$+ | 11.5 % |

This example shows that the catalysts under consideration are capable of carrying out reactions involving alkylation of paraffins with olefins.

It is readily apparent that the examples of practical application described in the foregoing have been given solely by way of explanatory illustration and that many modifications and variations could be made by those versed in the art without thereby departing either from the scope or the spirit of the invention.

What we claim is:

1. A method for the isomerization of paraffins in which the paraffins are brought into contact under conditions suited to the isomerization with a catalytic composition which comprises a mixture of (1) a Lewis acid corresponding to the formula MX$m$ in which:

M is an atom of a metal belonging to Groups IV, V and VI of the Periodic Table of Elements, X is a halogen, $m$ is within the range of 3 to 6, and (2) an acid corresponding to the formula C$_N$F$_{(2n+1)}$SO$_3$H in which $n$ is within the range of 2 to 8, and recovering isomerized paraffins from said contact.

2. A method according to claim 1, wherein the catalytic composition is introduced into said contact of the conversion process in the liquid state.

3. A method according to claim 2, wherein the catalyst composition is introduced into said contact impregnated on a support.

4. A method according to claim 3, wherein said support is selected from the group consisting of calcium fluoride, aluminum trifluoride, fluorinated carbon and polytetrafluoroethylene.

5. A method according to claim 1, wherein the catalyst comprises a mixture of antimony pentafluoride and an acid having the formula $C_NF_{(2N+1)}SO_3H$, where $n$ is within the range of 2 to 8.

6. A method of conversion according to claim 1, wherein n-pentane is isomerized to isopentane and said contact is performed while heating between −10° and 100° C in the presence of hydrogen.

7. The method of claim 1, wherein from 0.1 to 10 mols of Lewis acid is used per mol of the acid corresponding to the formula $C_NF_{(2n+1)}SO_3H$.

8. A method for the isomerization of paraffins in which the paraffins are brought together under conditions suited to the isomerization with a catalytic composition which comprises a mixture of
1. a Lewis acid corresponding to the formula $MXm$ in which:

M is an atom of a metal belonging to Groups IV, V and VI of the Periodic Table of Elements, X is a halogen, $m$ is within the range of 3 to 6,
and (2) an acid corresponding to the formula $RF(SO_3H)p$ where RF represents a perfluorinated alkyl or cycloalkyl hydrocarbon radical having a number of carbon atoms ranging from 2 to 8 and $p$ is within the range of 1 to 2, and recovering isomerized product from said contact.

9. A method according to claim 8, wherein the catalyst comprises a mixture of antimony pentafluoride and an acid having the formula $RF(SO_3H)p$.

10. The method of claim 8, wherein from 0.1 to 10 mols of Lewis acid is used per mol of the acid corresponding to the formula $RF(SO_3H)p$.

11. The method of claim 10, wherein n-pentane is isomerized to iso-pentane and said contact is performed while heating between −10° and 100° C in the presence of hydrogen.

12. A method for the alkylation of paraffins with olefins in which the paraffins are brought into contact under conditions suited to the alkylation with a catalytic composition which comprises a mixture of (1) a Lewis acid corresponding to the formula $MXm$ in which:

M is an atom of a metal belonging to Groups IV, V and VI of the Periodic Table of Elements, X is a halogen, $m$ is within the range of 3 to 6, and (2) an acid corresponding to the formula $C_NF_{(2n+1)}SO_3H$ in which $n$ is within the range of 2 to 8, and recovering alkylate product from said contact.

13. A method for the alkylation of paraffins with olefins in which the paraffins are brought together under conditions suited to the alkylation with a catalytic composition which comprises a mixture of (1) a Lewis acid corresponding to the formula $MXm$ in which:

M is an atom of metal belonging to Groups IV, V and VI of the Periodic Table of Elements, X is a halogen, $m$ is within the range 3 to 6, and (2) an acid corresponding to the formula $RF(SO_3H)p$ where RF represents a perfluorinated alkyl or cycloalkyl hydrocarbon radical having a number of carbon atoms ranging from 2 to 8 and p is within the range of 1 to 2, and recovering alkylate product from said contact.

14. A method for the alkylation of isoparaffins with olefins in which the isoparaffins and olefins are brought into contact under conditions suited to the alkylation with a catalytic composition which comprises a mixture of (1) a Lewis acid corresponding to the formula $MXm$ in which:

M is an atom of a metal belonging to Groups IV, V and VI of the Periodic Table of Elements, X ix a halogen, $m$ is within the range of 3 to 6, and (2) an acid corresponding to the formula $C_NF_{(2n+1)}SO_3H$ in which $n$ is within the range of 2 to 8, and recovering alkylate product from said contact.

15. A method for the alkylation of isoparaffins with olefins in which the isoparaffins and olefins are brought together under conditions suited to the alkylation with a catalytic composition which comprises a mixture of (1) a Lewis acid corresponding to the formula $MXm$ in which:

M is an atom of a metal belonging to Groups IV, V and VI of the Periodic Table of Elements, X is a halogen, $m$ is within the range of 3 to 6, and (2) an acid corresponding to the formula $RF(SO_3H)p$ where RF represents a perfluorinated alkyl or cycloalkyl hydrocarbon radical having a number of carbon atoms ranging from 2 to 8 and $p$ is within the range of 1 to 2, and recovering alkylate product from said contact.

* * * * *